United States Patent
Nakano et al.

(10) Patent No.: US 8,522,605 B2
(45) Date of Patent: Sep. 3, 2013

(54) WATER QUALITY ASSESSMENT SENSOR, WATER QUALITY ASSESSMENT METHOD FOR FEED WATER USING WATER QUALITY ASSESSMENT SENSOR, AND OPERATION MANAGEMENT METHOD FOR WATER TREATMENT FACILITY

(75) Inventors: Keiko Nakano, Yokohama (JP); Shinichi Taniguchi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 381 days.

(21) Appl. No.: 12/819,908

(22) Filed: Jun. 21, 2010

(65) Prior Publication Data
US 2010/0319441 A1 Dec. 23, 2010

(30) Foreign Application Priority Data
Jun. 22, 2009 (JP) ................. 2009-147183

(51) Int. Cl.
*G01N 15/06* (2006.01)
(52) U.S. Cl.
USPC ........................................ 73/61.75
(58) Field of Classification Search
USPC .................. 73/61.75, 64.53, 64.56
See application file for complete search history.

(56) References Cited

U.S. PATENT DOCUMENTS

| | | | | |
|---|---|---|---|---|
| 6,017,459 A | * | 1/2000 | Zeiher et al. | 210/650 |
| 7,165,452 B2 | * | 1/2007 | Kobayashi | 73/580 |
| 7,186,331 B2 | * | 3/2007 | Maartens et al. | 210/90 |
| 2006/0053870 A1 | * | 3/2006 | Berndt | 73/61.75 |
| 2009/0266762 A1 | | 10/2009 | Ito et al. | |

FOREIGN PATENT DOCUMENTS

| | | |
|---|---|---|
| JP | 2004-163185 A | 6/2004 |
| JP | 2005-106516 A | 4/2005 |
| JP | 2006-317163 A | 11/2006 |
| JP | 2009-240902 A | 10/2009 |
| WO | WO 2008/038575 A1 | 4/2008 |

* cited by examiner

*Primary Examiner* — Hezron E Williams
*Assistant Examiner* — Nathaniel Kolb
(74) *Attorney, Agent, or Firm* — Crowell & Moring LLP

(57) ABSTRACT

The same phenomenon as the phenomenon that a component of feed water is adsorbed to the surface of the membrane is used to assess water quality. Specifically, a sensor whose surface has a thin layer made of the same material as the material of the surface of the membrane and which includes a measurement unit such as a quartz crystal sensor that measures an adsorption rate on the thin layer is used to assess an effect of the water quality of the feed water on the membrane on the basis of a change in the adsorption rate on the sensor surface.

13 Claims, 3 Drawing Sheets

FRONT VIEW

SECTIONAL VIEW

WATER QUALITY ASSESSMENT SENSOR, WATER QUALITY ASSESSMENT METHOD FOR FEED WATER USING WATER QUALITY ASSESSMENT SENSOR, AND OPERATION MANAGEMENT METHOD FOR WATER TREATMENT FACILITY

CLAIM OF PRIORITY

The present application claims priority from Japanese patent application No. 2009-147183, filed on Jun. 22, 2009, the content of which is hereby incorporated by reference into this application.

BACKGROUND OF THE INVENTION

1. Field of the Invention

The present invention relates to water quality measurement for assessing an effect of water, which is fed to a water treatment membrane, on occlusion of the membrane.

2. Description of the Related Art

Various kinds of membranes are used to separate a component contained in water. There are two water filtration methods using the membrane. One of the methods is a dead-end filtration method or a method of passing an entire volume of feed water through a membrane. A component having failed to pass through the membrane is accumulated on the membranous surface. The other method is a cross flow filtration method, wherein water flows in parallel with the membranous surface and part of the water passes through the membrane. Among the membranes, a microfiltration membrane, an ultrafiltration membrane, a nanofiltration membrane, and a reverse osmosis membrane may be used for cross flow filtration. According to an ideal cross flow filtration method, a permeated water volume takes on a certain value determined with a water flow velocity but does not depend on an operation time. A component of raw water that does not permeate through a membrane is condensed and discharged. In contrast, according to the dead-end filtration method, a component of raw water that does not permeate through a membrane is accumulated. Therefore, a permeated water volume decreases along with the passage of an operation time. This phenomenon is called fouling. Even in the cross flow filtration method, since the component is adsorbed by the membrane, a phenomenon that the permeated water volume decreases is manifested. The phenomenon is also called fouling.

A related art will be described below by taking a reverse osmosis membrane, which is employed in advanced wastewater treatment, for instance. A semipermeable membrane is adopted as the surface of the reverse osmosis membrane, and the material thereof falls broadly into a cellulose triacetate series and an aromatic polyamide series. The membrane made of either of the materials allows only water to pass through by utilizing for filtration a difference in intensity of interaction between water molecules and dissolved components, and is used for the purpose of removing electrolytes in water.

The reverse osmosis membrane made of the aromatic polyamide series has high water permeability and exhibits excellent electrolyte removing performance, and is therefore widely used for industries. As for the structure of the reverse osmosis membrane, the structure of a complex membrane having a polyamide membrane, which has a thickness of 0.1 μm or less, formed on a microporous support whose thickness ranges from several tens of micrometers to several hundreds of micrometers is often adopted. The reverse osmosis membrane is used to remove dissolved organic substances or electrolytes during desalination of seawater, manufacture of pure water necessary to fabricate precision electronic devices such as semiconductors, advanced clean water treatment, or final treatment of wastewater or drainage.

For the final treatment of wastewater among the foregoing usages, water is generally fed to a reverse osmosis membrane through a treatment process described below. First, bulk trash and refuse contained in wastewater are removed through a screen. Thereafter, microscopic suspended substances including sand are settled in a sedimentation tank by applying, if necessary, a coagulant or the like and thus separated. Suspended solids and dissolved organic substances are contained in supernatant water, and are therefore biodegraded using microorganisms. Metabolites of the microorganisms are generated as sludge, and the sludge and water are separated from each other while being sedimented in the sedimentation tank or being passed through a microfiltration membrane. A primary effluent of the thus treated wastewater hardly contains suspended solids. In this state, disinfection or the like is performed in order to purify the effluent to such an extent that the water quality becomes high enough to sluice the effluent to a river. In Japan, in this state, treated wastewater is sluiced to a river, and water circulation is accomplished by utilizing natural purification. However, the Middle East, continental inland, or an island devoid of a river does not have a river or lake large enough to achieve the natural purification. Therefore, there is an increasing demand for reuse of the primary effluent of wastewater as drinkable water or industrial water by further purifying the effluent. The reverse osmosis membrane is used to remove dissolved organic substances or electrolytes from the primary effluent of wastewater during final treatment.

The primary effluent of wastewater contains organic substances that are measured as a total organic carbon (TOC) content ranging from 5 mg/L to 20 mg/L, though it varies depending on treatments performed in stages ending with a preceding stage. When the organic substances are separated from water using the reverse osmosis membrane, the organic substances can be reduced down to 1 mg/L or less. The TOC content is one of indices signifying water quality, indicates a total content of carbon in an organic compound among carbon compounds dissolved in water, and represents the total content of organic substances without identifying the components.

The reverse osmosis membrane employed in final wastewater treatment may be folded like a shape called a spiral or formed like a hollow fiber in order to increase a membranous surface area in a module. The spiral structure has a saclike reverse osmosis membrane fixed to the central core portion thereof and has it furled like an umbrella and stored in a cylinder. The mainstream of the module has a cylindrical shape having a diameter of 4 or 8 inches and a length of 1 m.

Adsorbates on a membranous surface include scales deposited due to a rise in the concentration of electrolytes in the vicinity of the membranous surface, a bio-fouling caused by microorganisms grown on the membranous surface, and an organic fouling caused by adsorption of organisms. The adsorbates are removed by regularly pouring cleansing water to the membranous surface or by utilizing a shearing stress. However, when organic substances are adsorbed by the membranous surface, they cannot be fully removed by the shearing stress but are gradually accumulated to make it necessary to replace the reverse osmosis membrane module with a new one. When the reverse osmosis membrane module is replaced with a new one, it is necessary to cease operation for a prolonged period of time. In addition, since the reverse osmosis membrane module cannot be recycled, the reverse osmosis membrane module has to be replaced with a new one. This leads to a cause of an increase in a running cost.

In the past, a fouling index (FI) value has been used as a water quality assessment method for predicting a fouling on a reverse osmosis membrane. The FI value may be called a silt density index (SDI) value. An FI value measurement method is stipulated in the JIS K 3802. Namely, water is passed through a filter, which has bores of 0.45 μm in diameter and has a diameter of 47 mm, at 206 kPa according to the dead-end filtration method, and a ratio of a time necessary to filter 500 ml in an initial stage to a time necessary thereto after the water is passed for fifteen min is calculated as the FI value. Manufacturers of the reverse osmosis membrane determine the upper limit of the FI values of feed water, and demand that the FI value should range from 3 to 4.

SUMMARY OF THE INVENTION

The FI value is used to design a reverse osmosis membrane facility or assess feed water. Even when the FI value is equal to or smaller than the demanded specification, time-sequential deterioration due to an organic fouling may proceed quickly. This is attributable to a difference in a phenomenon to be measured. Specifically, for a reverse osmosis membrane, the cross flow method is adopted as a filtration method, and a decrease in a water permeation velocity results from the fact that dissolved components are adsorbed to or accumulated on a membranous surface through chemical interaction. In contrast, for the measurement of the FI value, the velocity at which occlusion of bores by trash occurs is assessed using the dead-end filtration method.

Unless an effect of the quality of feed water on a fouling can be assessed, when a reverse osmosis membrane facility is newly designed, the number of reverse osmosis membrane modules and a replacement frequency cannot be estimated. An operation load on the reverse osmosis membrane cannot be reduced by feeding back the result of the assessment so as to determine a condition for treatment of microorganisms, which is a treatment preceding filtration through the reverse osmosis membrane, during operation.

In efforts to solve the foregoing problem, Japanese Unexamined Patent Application Publication No. 2005-106516 has disclosed a method in which feed water supposed to be fed to a reverse osmotic member is passed through a membrane, and a volume of adsorbates is measured instead of a passing velocity. However, the method makes it necessary to temporarily extract the adsorbates on the membrane, and the material of the membrane employed in the assessment is different from the material of the surface of the reverse osmosis membrane. Japanese Unexamined Patent Application Publication No. 2006-317163 has disclosed a method in which a reverse osmosis membrane module to be accelerated for prediction of a fouling is incorporated in a facility in order to predict a deteriorating situation of another reverse osmosis membrane module. According to the method, since deterioration of the reverse osmosis membrane for measurement progresses quickly, a replacement frequency rises and a cost increases. In addition, the reverse osmosis membrane module cannot be incorporated in an existing facility afterward.

In order to solve the problem, it is necessary to assess water quality by utilizing the same phenomenon as the phenomenon used to predict an organic fouling. In the case of the organic fouling, chemical interaction between dissolved organic substances and a material of a membranous surface is dominant. Therefore, interaction between a material identical or similar to the surface material and dissolved components contained in water to be assessed, or more particularly, an adsorption rate should be inspected.

In the present invention, a sensor having the surface thereof coated with a material similar to the material of a membrane for separation is used to assess an effect of the quality of feed water on a fouling on the basis of a change in an adsorption rate on the sensor surface or a change in the concentration of organisms in water between the water lying in front of the sensor and the water lying behind the sensor.

At this time, organic components of water to be fed to a reverse osmosis membrane are as dilute as a total organic carbon (TOC) content ranging from 5 mg/L to 20 mg/L. Therefore, an adsorption rate on the membrane per a short period of 30 min or less is equal to or smaller than 1 μg/cm², and is hard to detect by performing normal gravimetric measurement, membranous surface analysis, or concentration change measurement.

As one of measurement methods, there is a method of measuring a microscopic adsorption rate using a quartz crystal sensor. The quartz crystal sensor is a sensor that has an electrode formed in quartz having a thickness of 1 mm or less and measures a weight on the basis of a resonant frequency thereof observed when given a straining vibration. The resonant frequency is determined with the thickness of the quartz. When the sensor gets heavier because substances have adhered to the surface thereof, the resonant frequency thereof is shifted to be lower. The relationship between the resonant frequency and adsorption rate is expressed with the Sauerbrey's equation 1 presented below.

$$\Delta m = -(\mu q \rho q)^{1/2} \cdot \Delta f / 2 fo \quad \text{(Equation 1)}$$

where $\Delta m$ denotes an adsorption rate on a sensor surface, $\Delta f$ denotes a degree of a change in a frequency, and $\Delta q$ denotes a shearing stress of quartz that is $2.947 \times 10^{10}$ kg/m·s². In addition, $\rho q$ denotes the density of quartz that is 2648 kg/m³, and fo denotes an initial resonant frequency of quartz. When a quartz crystal sensor whose initial resonant frequency is 5 MHz (the thickness of a quartz plate is 0.3 mm) is employed, a change of 1 Hz is associated with an adsorption rate of 17.7 ng/cm².

A thin layer made of the material of a membrane for separation is formed on one side of a quartz crystal sensor, whereby the sensor for the separation membrane to be assessed is completed. As a membrane forming method, there are a method in which a solution having the material of the separation membrane dissolved therein is used to form a membrane according to a technique such as spin coating, printing, or dipping, a method of forming a membrane through dry processing such as deposition, a method of transferring an Langmuir-Blodgett (LB) membrane or a membrane, which is formed on a liquid-level surface through interfacial polymerization, to a sensor, and a method of causing monomers to react on a sensor surface for polymeric synthesis. At this time, the membrane thickness should preferably be equal to or smaller than 100 nm for fear a measurable maximum value of the sensor may be exceeded.

The resonant frequency of quartz is largely affected by temperature. A measuring position has to have temperature thereof controlled, and a temperature change has to be equal to or smaller than 1° or preferably 0.1°. For measurement, any of a method of measuring the resonant frequency off-line after collecting water, an in-line method of forming a bypass in a pipe of water to be assessed, and feeding water to a measuring position at which measurement is performed using a quartz crystal sensor, and a method of placing a sensor alone in a water treatment facility after measuring an initial value of the resonant frequency of the sensor, and regularly taking out the sensor so as to inspect a change in the resonant frequency may be selected according to a purpose such as initial assessment of feed water, feedback control for determination of a condition for line operation, or prediction of a fouling on a membrane.

The quartz crystal sensor has been described so far. As long as a method of measuring an adsorption rate employs a sensor having the surface thereof coated with the material of a membrane, surface plasmon resonance, surface reflectance change measurement, or absorbance measurements to be performed in front of a sensor and behind the sensor will do.

As for a membrane to be placed downstream of water whose quality has been assessed, the invention has been described by taking for instance a reverse osmosis membrane for advanced wastewater treatment. The usage of the reverse osmosis membrane is not limited to the advanced wastewater treatment. The reverse osmosis membrane may be applied to quality assessment of feed water to be performed in the course of desalination of seawater, manufacture of pure water employed in fabrication of precision electronic devices such as semiconductors, or advanced clean-water treatment. Further, especially when the cross flow filtration method is adopted, the other membranes including a microfiltration membrane, an ultrafiltration membrane, and a nanofiltration membrane are confronted with, in addition to a problem that bores are physically occluded, a problem that components adhering to a surface through chemical interaction degrade permeability. There is therefore a demand for an assessment technique to be substituted for the FI value. According to the present invention, water quality can be assessed.

According to a water quality assessment method in which the present invention is implemented, whether feed water is good can be readily assessed in relation to degradation in performance of a membrane derived from a fouling on the surface of the membrane. Therefore, excess specifications are unnecessary to design a membrane facility. The membrane can be operated stably for a prolonged period of time by performing feedback to pretreatment of the membrane. Further, the membrane replacing timing or cleansing timing can be predicted in consideration of a change in water quality.

BRIEF DESCRIPTION OF THE INVENTION

Embodiments of the present invention will be described in detail based on the following figures, wherein.

DESCRIPTION OF THE PREFERRED EMBODIMENTS

The present invention will be concretely described below by citing embodiments.

[Embodiment 1]

Figure 1:
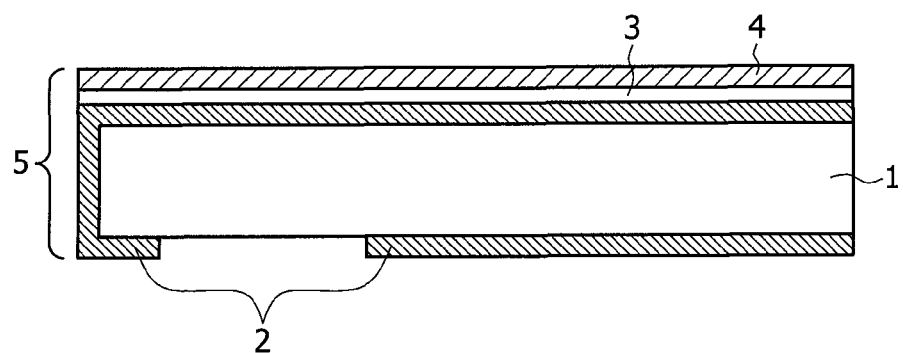
FIG. 1 is a sectional view of a sensor employed in water quality assessment in accordance with an embodiment of the present invention.

FIG. 1 is a sectional view of a quartz crystal sensor in accordance with an embodiment of the present invention. A gold electrode 2 having a thickness of 300 nm was formed on both the sides of a quartz plate 1, which had a thickness of 0.3 mm and a diameter of 14 mm, through sputtering. Further, a silicon oxide was sputtered to an adsorption measuring surface in order to form a silicon oxide layer 3 of 100 nm thick. The back side was protected with protection tape, and then immersed in an ethanol solution, which contains 1% of 3-aminopropyltrimethoxysilane, for two min. Thus, the surface of the silicon oxide layer 3 had undergone amino-terminal silane coupling.

As a model material of a reverse osmosis membrane, aromatic polyamide (chemical 2) obtained by polymerizing m-phenylenediamine and terephtalic acid (chemical 1) was used to modify the sensor. The method will be described below. The sensor is put in an aqueous solution containing 0.5% of m-phenylenediamine, and a telephthalic acid hexane solution (saturating concentration) is poured into the aqueous solution. The sensor is hoisted in order to transfer a polyamide membrane, which is polymerized on the interface between the aqueous solution and hexane solution, to the sensor. Thereafter, the sensor is heated at 80° C. for two min in order to upgrade the adhesiveness between the sensor surface and polyamide membrane. The thickness of the polyamide membrane 4 on the sensor was 90 nm.

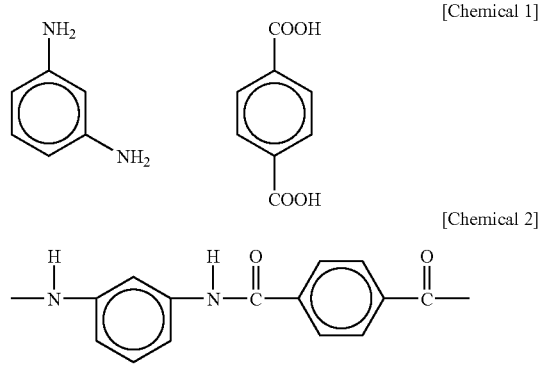

[Chemical 1]

[Chemical 2]

As water whose quality is assessed, a primary wastewater effluent whose TOC content is 3.5 mg/L and a phenylalanine aqueous solution whose TOC content is 5 mg/L were prepared. These waters cannot be discriminated from each other on the basis of the FI values, but are largely different from each other in terms of an adsorption/accumulation velocity on a reverse osmosis membrane.

The waters were caused to flow into the sensor surface at a flow velocity of 0.2 ml/min/cm$^2$, and adsorption rates were measured. The adsorption rate of the primary wastewater effluent measured in ten min was 150 ng/cm$^2$, and the adsorption rate of the phenylalanine aqueous solution was 50 ng/cm$^2$. Thus, the primary wastewater effluent was assessed as water that tends to cause a fouling on the reverse osmosis membrane. In the present embodiment, the adsorption or accumulation rate can be measured in line with an environment for the cross flow method.

[Embodiment 2]

A sensor having the same structure as the sensor of the embodiment 1 and employing a membrane other than the polyamide membrane 4 was assessed. (a) A silicon oxide (SiO$_2$) membrane of 100 nm thick was formed on an adsorption measuring surface of a quartz crystal, which has a thickness of 0.3 mm and a diameter of 14 mm and has a gold electrode of 300 nm thick formed on both sides thereof through sputtering, by performing sputtering. (b) A polyamide membrane was formed on the silicon oxide layer of 100 nm thick according to the same method as that in the embodiment 1. (c) A polyimide membrane was formed on the gold electrode. Thus, three quartz crystal sensors were prepared. As for polyimide, a polyimide solution PIX-L110SX manufactured by Hitachi Chemical Co., Ltd. was diluted with N-methylpyrolidone to be ten times larger in volume. After polyimide was spin-coated, it was hardened using a hot plate heated at 200° C. The membrane thickness is 180 nm.

A wastewater effluent was poured to the surfaces of the sensors at a flow velocity of 0.2 ml/min/cm$^2$, and adsorption rates were measured. (a) The adsorption rate on the silicon oxide membrane measured ten min later was equal to or smaller than 10 ng/cm$^2$. (b) The adsorption rate on the polyamide membrane having a structure similar to the reverse osmosis membrane was 150 ng/cm$^2$. (c) The adsorption rate on the polyimide membrane was 400 ng/cm$^2$. (a) An effect of the silicon oxide membrane on a fouling was underestimated. (c) An effect of the polyimide membrane on a fouling was overestimated. This reveals that a sensor surface has to be made of the same material as the material of the surface of a membrane for separation to be estimated. As for the same material, the material of the membrane on the sensor surface may not be identical to the material of the separation membrane but may be a similar material permitting the adsorption rate of the sensor surface to be on a level with that of the separation membrane.

[Embodiment 3]

Figure 2:
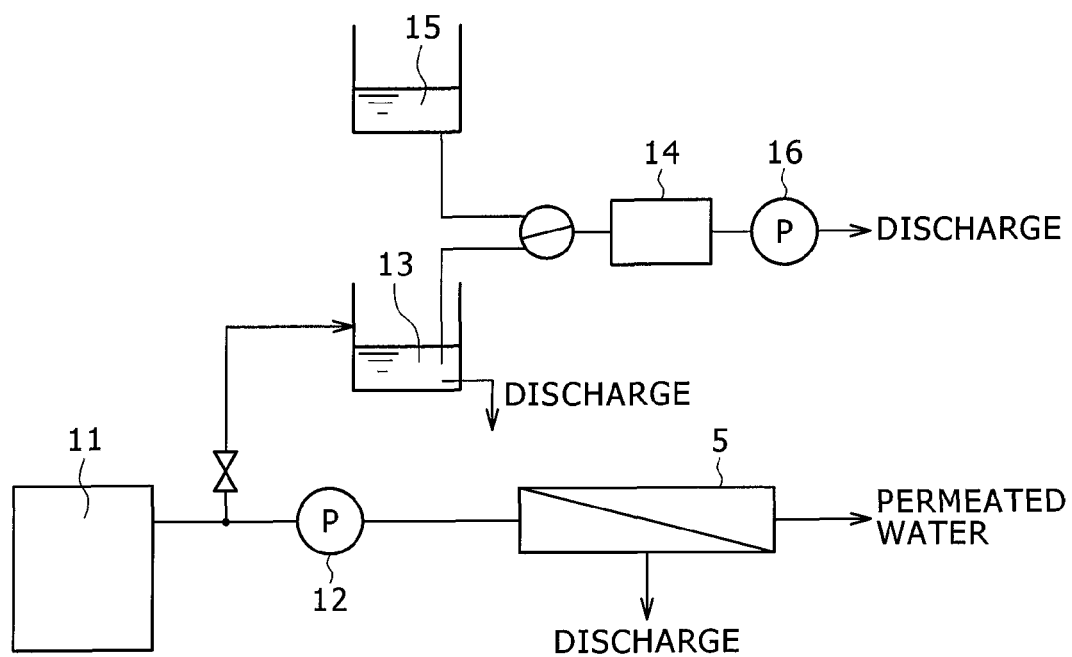
FIG. 2 shows the outline of an in-line water quality assessment system.
Figure 3:
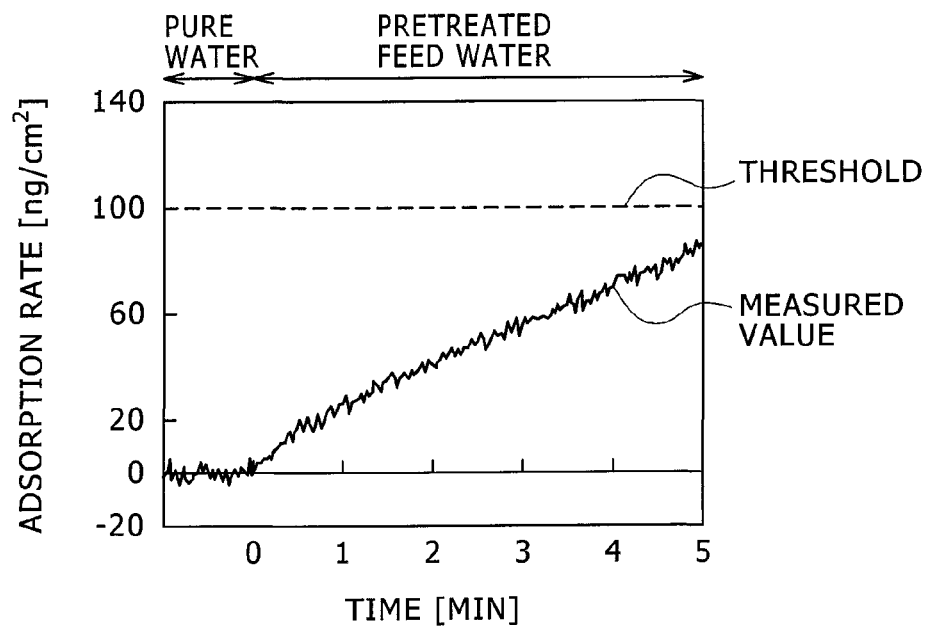
FIG. 3 shows an example of in-line adsorption rate measurement.

FIG. 2 shows an embodiment of a system for measuring water quality in-line. In FIG. 2, a treatment tank 11 in which an adsorbent is put is included for pretreatment of a reverse osmosis membrane 10, and water quality having undergone the pretreatment is assessed in-line and fed back for determination of an operating condition for the pretreatment. A branch is formed upstream of a pressurization pump 12, which precedes the reverse osmosis membrane 10, in order to route water to a measuring apparatus. The branch is provided with a valve. For measurement, the valve is opened in order to introduce branched water to a water buffer 13. Pure water (TOC: 0.1 mg/L or less) 15 is fed to an adsorption rate measurement unit 14 in order to keep a sensor surface stable. Thereafter, channels are switched. Water is extracted from the water buffer 13 using a peristaltic pump 16, and fed to the adsorption rate measurement unit 14. At this time, a flow rate for feeding is identical to a flow rate on the surface of the reverse osmosis membrane. The membranous-surface flow rate is a flow rate per unit area or unit hour at which water passes through the membranous surface, and ranges from 0.01 ml/min/cm$^2$ to 0.2 ml/min/cm$^2$. A surplus of a water tank and a drainage produced after water quality measurement are discharged to outside the system. FIG. 3 shows an example of measurement. After measurement is performed for five min, if a measured value is larger than a threshold adsorption rate (100 ng/cm$^2$ in FIG. 3), contamination on the reverse osmosis membrane is likely to occur. Therefore, an operating condition for pretreatment is controlled, for example, a flow velocity is decreased in order to extend a time during which the adsorbent and water are in contact with each other.

The adsorption rate measurement unit includes a sensor retainer, a water channel, an electrode for use in measuring the oscillatory or resonant frequency of a sensor, and a temperature control mechanism for keeping the water temperature and sensor temperature constant. The electrode is structured not to come into contact with water.

[Embodiment 4]

Figure 4:
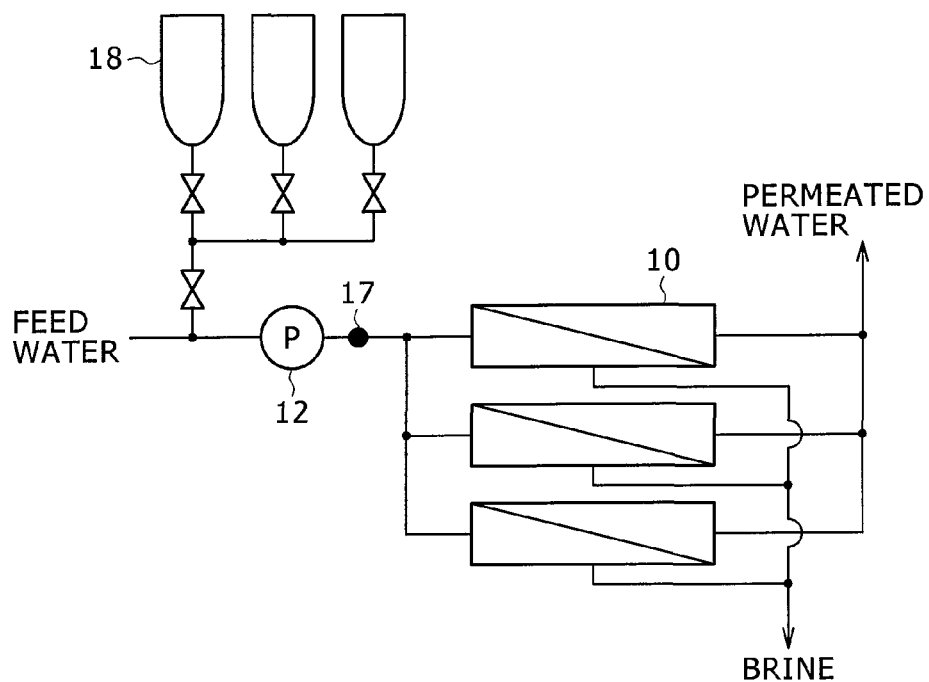
FIG. 4 shows the outline of a system for measuring a time-sequential change in a fouling on a membrane.
Figure 5:
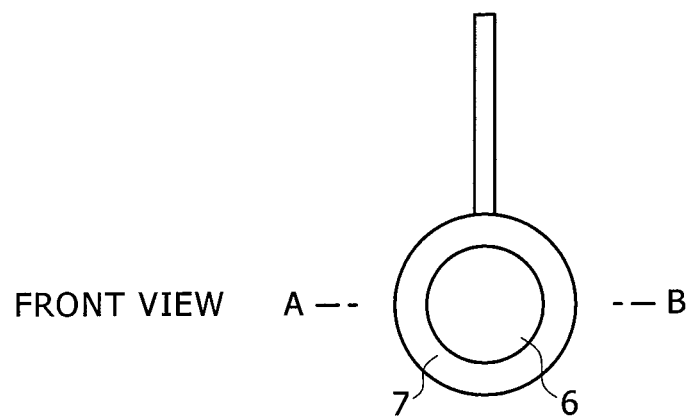
FIG. 5 includes a front view and a sectional view of an instrument for retaining a sensor in a pipe.
Figure 5:
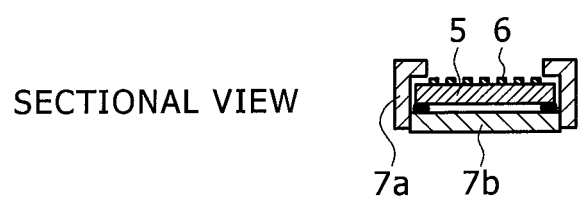

FIG. 4 shows a system for measuring a time-sequential change in a membranous fouling volume so as to predict contamination on a membrane. A reverse osmosis membrane module 10 has the surface thereof cleansed with permeated water or an agent 18 after being operated for a certain period of time. Feed water or a chemical agent to a reverse osmosis membrane is pressurized and fed by a pressurization pump 12. For monitoring of the situation, a sensor having the surface thereof modified with the same material as the reverse osmosis membrane is retained at a position 17 succeeding the pressurization pump. FIG. 5 shows an embodiment of a sensor retainer. A retainer 7 is used to bring only the adsorption rate measuring surface of a sensor 5 into contact with water. In order to prevent contamination or adhesion on or to the back side of the sensor, the retainer 7 is separated into two regions 7a and 7b. The sensor is pressed against the region 7a by the region 7b and an O ring. The back side of the sensor does not come into contact with a fluid. A spiral reverse osmosis membrane module is provided with a spacer for preventing the membranous surface from coming into contact with the fluid and preserving a channel. Since disturbance of a water flow by the spacer affects a membranous fouling, the spacer 6 is placed on the sensor surface.

The sensor is taken out once a week, and an adsorption rate on the surface is measured off-line. At this time, the measurement is performed in the air. In order to eliminate an effect of adsorbed water, the sensor is heated at 120° for five min and the sensor surface is dried. Thereafter, the sensor is mounted in a quartz crystal microbalance measuring apparatus, and the resonant frequency of the sensor is measured. After the measurement, an adsorption rate is estimated based on a difference from an initial resonant frequency.

At this time, since the sensor is mounted in and dismounted from the measuring apparatus, the precision in repeated measurements of the resonant frequency has a significant meaning. Therefore, the sensor was mounted and dismounted in order to repeatedly measure the resonant frequency. A variance among measured values was estimated. This revealed that when the sensor was mounted and dismounted, the variance σ was 0.23 μg/cm$^2$. The adsorption rate on the reverse osmosis membrane is estimated to range from about 10 μg/cm$^2$ to about 50 μg/cm$^2$ a week, the adsorption rate can be measured with satisfactory precision.

The reverse osmosis membrane module has a length of 1 m. In practice, after a fouling occurs on an upstream side, the fouling proceeds to a downstream side. Permeability decreases accordingly. The sensor is used to simulate the upstream fouling. According to the method of the present invention, before a decrease in permeability due to a fouling occurs in the reverse osmosis membrane module, the situation of the fouling can be predicted.

The situation of the fouling on the sensor as well as the pressure of the operated pump is monitored, and fed back to determine an operating condition for activated sludge treatment that is pretreatment or used to determine the cleansing timing of the reverse osmosis membrane.

What is claimed is:

1. A water quality assessment sensor for assessing water quality, comprising:
   an adsorption thin layer coated to an adsorption measuring surface of the sensor; and
   a measuring apparatus for measuring an adsorption rate on the adsorption thin layer,
   wherein
     water to be assessed is water that has not been separated by a water treatment membrane,
     material of the adsorption thin layer is identical to that of the water treatment membrane, and the adsorption thin layer is less than or equal to 100 nm thick.

2. The water quality assessment sensor according to claim 1, wherein the membrane whose material is identical to that of the adsorption thin layer is a nanofiltration membrane or reverse osmosis membrane whose bores have a diameter of 10 nm or less.

3. The water quality assessment sensor according to claim 1,
wherein: a quartz crystal sensor is included as the measuring apparatus;
the adsorption thin layer is disposed on the quartz crystal sensor; and
the adsorption rate on the adsorption thin layer is measured based on a resonant frequency of the quartz crystal sensor.

4. The water quality assessment sensor according to claim 3, wherein the sensor is a quarts crystal sensor having a reference resonant frequency that ranges from 3 MHz to 30 MHz, and the adsorption rate is measured based on a degree of a change in the resonant frequency.

5. The water quality assessment sensor according to claim 1, wherein the measuring apparatus performs any of surface plasmon resonance, surface reflectance change measurement, and absorbance measurement.

6. The water quality assessment sensor according to claim 1, further comprising a temperature controller.

7. The water quality assessment sensor according to claim 1, wherein the adsorption thin layer and measuring apparatus are freely mounted or dismounted.

8. The water quality assessment sensor according to claim 1, wherein the material of the adsorption thin layer is aromatic polyamide.

9. A feed water assessment method for assessing a component of feed water to be fed to a water treatment membrane, comprising the steps of:
using the water assessment sensor according to claim 1; and
measuring an adsorption rate on the sensor, after a surface of the sensor is brought into contact with the feed water.

10. The feed water assessment method according to claim 9, wherein the feed water to be fed to the membrane is branched, and the branched feed water is brought into contact with the sensor.

11. The feed water assessment method according to claim 9, wherein the sensor is disposed in a water channel upstream of the membrane.

12. The feed water assessment method according to claim 9, wherein after the sensor is brought into contact with pure water, the sensor is brought into contact with feed water that is an object of assessment.

13. An operation management method for a water treatment facility employing a membrane, comprising the steps of:
assessing feed water to be fed to the membrane using the sensor according to claim 1 disposed upstream of the membrane and having the surface thereof coated with the same material as the material of the surface of the membrane; and
managing the operations of the member and the facility located upstream of the membrane based on the result of the assessment.

* * * * *